United States Patent [19]
Wallace et al.

[11] Patent Number: 5,618,410
[45] Date of Patent: Apr. 8, 1997

[54] AUTOMATICALLY DRAINING VACUUM APPARATUS

[75] Inventors: George M. Wallace, Willow Grove; Terence L. Snyder, Downingtown, both of Pa.

[73] Assignee: Den-Tal-Ez, Inc., Audubon, Pa.

[21] Appl. No.: 388,856

[22] Filed: Feb. 15, 1995

[51] Int. Cl.⁶ .............................. B01D 21/24; A47L 5/38
[52] U.S. Cl. ............................ 210/123; 15/353; 137/398; 137/429; 433/92
[58] Field of Search .................................. 210/121, 123, 210/125, 513; 137/433, 395, 398, 429; 433/91, 92; 15/314, 353, 422

[56] References Cited

U.S. PATENT DOCUMENTS

| | | |
|---|---|---|
| Re. 24,755 | 12/1959 | Winter . |
| Re. 32,027 | 11/1985 | Hyatt et al. ............... 417/368 |
| 184,461 | 11/1876 | Cooper . |
| 2,864,166 | 12/1958 | Shaw . |
| 3,012,322 | 12/1961 | Thompson . |
| 3,017,886 | 1/1962 | Thompson . |
| 3,078,579 | 2/1963 | Jones et al. . |
| 3,138,873 | 6/1964 | Bishop . |
| 3,240,000 | 3/1966 | Hayes et al. . |
| 3,291,508 | 12/1966 | Kolthoff, Jr. . |
| 3,457,645 | 7/1969 | Swanson . |
| 3,847,573 | 11/1974 | Gandrud ....................... 433/92 |
| 3,848,290 | 11/1974 | Bates ............................. 15/321 |
| 4,231,133 | 11/1980 | Probost ..................... 15/300 A |
| 4,475,264 | 10/1984 | Schulz ...................... 15/300 A |
| 4,564,374 | 1/1986 | Hofmann ....................... 433/92 |
| 4,651,380 | 3/1987 | Ogden ........................ 15/321 |
| 4,783,878 | 11/1988 | McCambridge ............. 15/327 D |
| 4,934,017 | 6/1990 | Kent ............................. 15/321 |
| 5,099,543 | 3/1992 | Wade ............................ 15/321 |
| 5,311,640 | 5/1994 | Holland ......................... 15/353 |

*Primary Examiner*—Joseph W. Drodge
*Attorney, Agent, or Firm*—Panitch Schwarze Jacobs & Nadel, P.C.

[57] ABSTRACT

An automatically draining vacuum apparatus for collecting a fluid to be vacuumed. The vacuum apparatus includes a vacuum generating source which generates a suction force and a tank for holding the fluid to be vacuumed. The tank includes a vacuum port, an inlet and a drainage opening for emptying fluid held within the tank. The suction force at the vacuum port draws the fluid to be vacuumed into the tank through the inlet and prevents the fluid within the tank from passing from the tank through the drainage opening. A float is located in the tank for closing off the vacuum port to prevent the fluid within the tank from passing through the vacuum port. The float has a positive buoyancy with respect to the fluid and is positioned within the tank such that when the fluid within the tank is above a predetermined level, the suction force at the vacuum port and the float buoyancy maintain the float in a blocking position to at least partially block the vacuum port, creating a second suction force. The second suction force, which is less than the first suction force in the tank, allows the fluid within the tank to drain to a level below the predetermined level to cause the float to move from the blocking position and restore the first suction force in the tank.

12 Claims, 3 Drawing Sheets

AUTOMATICALLY DRAINING VACUUM APPARATUS

FIELD OF THE INVENTION

The present invention relates to a vacuum apparatus having automatic drain provisions and, more particularly, to a dry vacuum apparatus for use as a dental aspirator in which fluid within a collection tank is automatically drained when the fluid reaches a predetermined level without significantly interfering with the aspirating process.

BACKGROUND OF THE INVENTION

Vacuum systems for collecting fluids or fluids containing particulate matter are generally known. One use for such vacuum systems is dental aspirators. Dental aspirators utilize a vacuum apparatus for removing saliva, broken teeth, bone chips, blood or filling materials from the mouth of a patient to allow a dentist to complete the procedure without continual interruptions for the patient to rinse. Dental aspirators are also used in other dental procedures where it is necessary to use a water pick or other device which continuously feeds additional fluid into the patient's mouth, which must be contemporaneously removed. Dental aspirators therefore serve two important functions; permitting a dentist to complete his work without interruption, and providing additional patient comfort during dental procedures.

The known dental aspirator systems generally use flexible evacuation hoses, which are inserted into a patient's mouth during surgery or other procedures. Each dental operatory of an office includes an evacuation hose which is connected to a common piping system. This common piping system is connected to a single, remotely located, vacuum apparatus that services all of the dental operatories.

One known vacuum apparatus has a collection tank, which contains a float to detect the fluid level in the tank. When the fluid reaches a predetermined level, the float blocks a vacuum port such that no additional fluid can be collected in the tank. The vacuum generating source is then turned off and the fluid collected in the tank is drained.

In another known vacuum apparatus, the float moves an actuator which turns off power to the vacuum generating source when the fluid in the tank reaches a predetermined level. When the power to the vacuum generating source is turned off, a valve is opened to drain the collected fluid.

One of the problems inherent in the above described vacuum apparatuses is that once the collection tank has been filled to the predetermined level, the vacuum generating source must be turned off in order for the collection tank to be drained. Whether the vacuum source is manually or automatically shut off and the tank drained, suction is lost in the operatories. The draining process can take five to fifteen minutes, during which time none of the aspirators in the dental operatories are functioning. This time delay interrupts the dentist's work and causes additional patient discomfort.

One solution to this problem is to provide a larger collection tank. However, in a large dental practice with several operatories, it is difficult to determine what collection tank volume is sufficient to provide uninterrupted aspirator service. In practice, a fifteen gallon collection tank has been found to be generally acceptable and generally needs draining only once a day, after the close of business hours. However, depending on the types of dental procedures performed, the collection tank can become filled during business hours, and the vacuum apparatus must be turned off and the tank drained, thereby interrupting the procedures being performed.

The present invention overcomes many of the disadvantages inherent in the above-described dental aspirator vacuum systems by providing an automatically draining vacuum apparatus in which the collection tank is partially drained when the fluid in the collection tank reaches a predetermined level. Vacuum service to the evacuation hoses in the dental operatories is only interrupted for ten to fifteen seconds during the automatic draining of the collection tank, allowing a dentist to continue his procedure without substantial interruption or additional discomfort to the patient.

SUMMARY OF THE INVENTION

Briefly stated, the present invention is an automatically draining vacuum apparatus for collecting a fluid to be vacuumed. The vacuum apparatus comprises a vacuum generating source which generates a suction force and a tank for holding the fluid to be vacuumed. The tank includes a vacuum port in fluid communication through a passage with the vacuum generating source for creating a first suction force in the tank. The tank further includes an inlet in fluid communication with the fluid to be vacuumed and a drainage opening for emptying fluid held within the tank. The first suction force draws the fluid to be vacuumed into the tank through the inlet and prevents the fluid within the tank from passing from the tank through the drainage opening. A float is located in the tank for closing off the vacuum port to prevent the fluid within the tank from passing through the vacuum port. The float has a positive buoyancy with respect to the fluid such that the float rises as the tank is filled with the fluid to be vacuumed and falls as the fluid within the tank is drained from the tank. The float is positioned within the tank such that when the fluid within the tank is above a predetermined level, the suction force at the vacuum port and the float buoyancy maintain the float in a blocking position to at least partially block the vacuum port, creating a second suction force. The second suction force, which is less than the first suction force in the tank, allows the fluid within the tank to drain to a level below the predetermined level thereby causing the float to move from the blocking position to restore the first suction force in the tank.

The present invention also includes a method for automatically draining a continuously operating vacuum apparatus for collecting a fluid to be vacuumed. The apparatus includes a vacuum generating source in fluid communication with a tank through a vacuum port. The method comprises the steps of:

(1) operating the vacuum generating source to draw the fluid to be vacuumed into the tank;

(2) detecting a level of fluid within the tank; and (3) draining fluid from the tank when the fluid reaches a predetermined level while operating the vacuum generating source.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE PREFERRED EMBODIMENT

Figure 1:
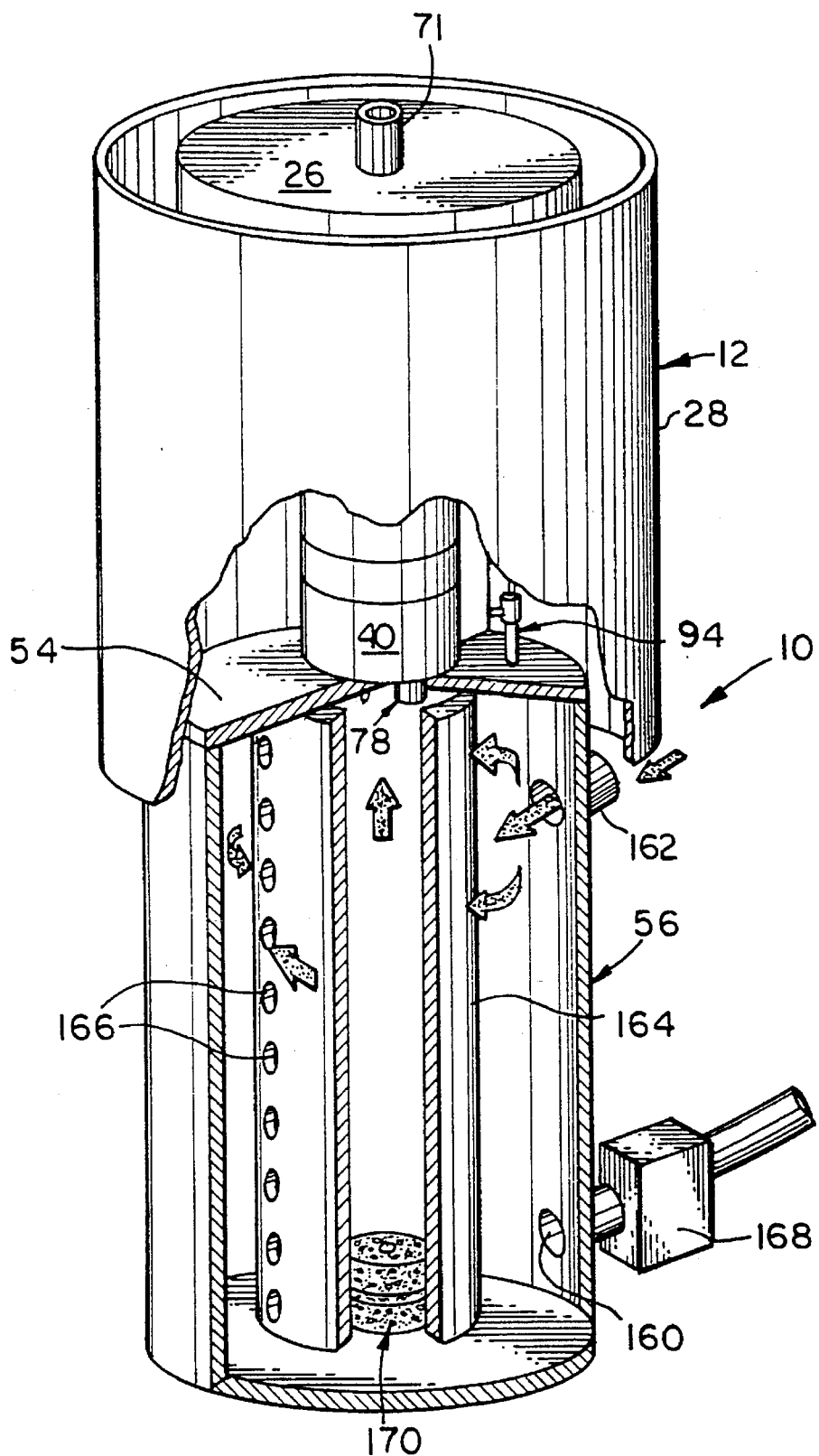
FIG. 1 is a perspective view, partially broken away into section, of an automatically draining vacuum apparatus in accordance with the present invention.

Certain terminology is used in the following description for convenience only and is not limiting. The words "right," "left," "upper" and "lower" designate directions in the drawings to which reference is made. The words "inwardly" and "outwardly" refer to directions toward and away from, respectively, the geometric center of the automatically draining vacuum apparatus and designated parts thereof. This terminology includes the words specifically mentioned above, derivatives thereof and words of similar import.

Referring to the drawings in detail, wherein like numerals indicate like elements throughout, there is shown in FIGS. 1–4 a preferred embodiment of an automatically draining vacuum apparatus for collecting a fluid to be vacuumed (not shown), generally designated 10, in accordance with the present invention. FIG. 1 is a perspective view of the automatically draining vacuum apparatus 10, hereinafter referred as the "vacuum apparatus" 10. In the preferred embodiment, the vacuum apparatus 10 is used in an aspirator system for collecting a fluid from dental operatories. However, it is understood by those skilled in the art from this disclosure that the vacuum apparatus 10 is suitable for other uses, such as a fixed canister vacuum system for collecting various fluids.

Figure 2:
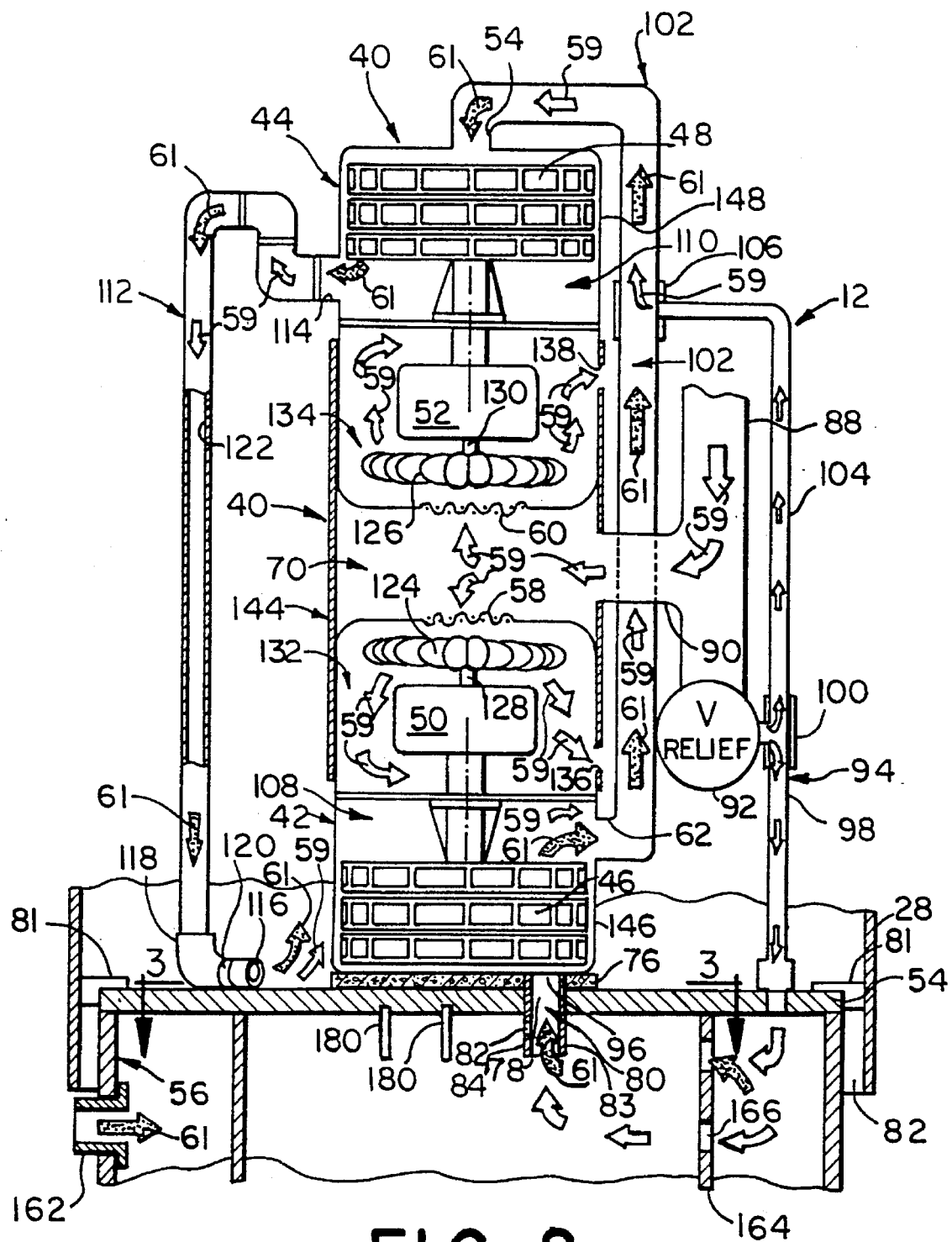
FIG. 2 is an enlarged schematic view, partially in cross-section, of a portion of the vacuum apparatus shown in FIG. 1.

Referring now to FIGS. 1 and 2, the vacuum apparatus 10 includes a vacuum generating source, generally designated as 12, which generates a suction force. In the presently preferred embodiment, the vacuum generating source 12 includes a power unit subassembly 40, shown in detail in FIG. 2, comprising two vacuum motor fan units, 42, 44 connected in a two-stage arrangement to generate the suction force. Each vacuum motor fan unit 42, 44 is provided with a blower 46, 48 and a motor 50, 52 drivingly connected to the blower 46, 48, respectively.

The vacuum motor fan units 42, 44 are mounted in an axially-aligned, vertically-stacked and reversed relation to each other by a sleeve 144 which extends between the end portions of the housings 146, 148. The sleeve 144 is in hermetically-tight engagement with the vacuum motor fan unit 42, 44 side walls to define the sealed plenum chamber 70. In the axially-aligned, vertically-stacked configuration, the motor cooling air inlets 58, 60 of the motors 50, 52 are located in the plenum chamber 70 confronting one another. Preferably, the sleeve 144 is formed from a resilient, elastomeric material. However, it is understood by those skilled in the art from this disclosure that other types of material, such as aluminum or steel could, be utilized for the sleeve.

As shown in FIG. 2, the blowers 46, 48 are located in blower chambers 108, 110 of the vacuum motor fan unit housings 146, 148, respectively. The first blower chamber 108 has an inlet 96 and an outlet 62. The second blower chamber 110 has an inlet 64 and an outlet 114. The suction force at the inlet 96 of the first fan unit 42 is increased by connecting the vacuum air outlet 62 of the first blower chamber 108 to the vacuum air inlet 64 of the second blower chamber 110 by a blower interconnect conduit 102. The outlet 114 of the second blower chamber 110 is connected by a an exhaust line 112 to a muffler 122. The exhaust line terminates at an outlet 116 of an elbow 118 which is held in position by clamp 120.

Referring now to FIGS. 1 and 2, a simplified air cooling circuit is used to enable the vacuum motor fan units 42, 44 to operate more efficiently. Cool outside air, represented by the arrows 59, is fed into an intake fitting 71 of an air filter assembly 26 which is removably mounted to an upper shroud 28 which surrounds the power unit subassembly 40. A cooling air supply pipe 88 is connected to an outlet fitting (not shown) of the air filter assembly 26. An intermediate laterally projecting conduit 90 connects the cooling air supply pipe 88 to the plenum chamber 70, located between the motor cooling air inlets 58 and 60. Internal ventilating fans 124, 126, for drawing air from the plenum 70 through the cooling air inlets 58, 60 into the motor chambers 132, 134, are connected to the motors 50, 52 by drive shafts 128, 130, respectively. Motor air outlets 136, 138, for exhausting the cooling air 59, are formed between the motor chambers 132, 134 of each vacuum motor fan unit 42, 44, respectively, and the surrounding space within the upper shroud 28.

As shown in FIG. 2, the cooling air supply pipe 88 is connected by a vacuum relief valve 92 and a tee fitting 100 to an auxiliary air conduit 94. The auxiliary cooling air conduit 94 includes an upper portion 104, which is connected by a second tee fitting 106 to the blower interconnecting conduit 102 to supply cooling air 59 to the vacuum air inlet 64 of the second blower 48, and a lower portion 98 of the auxiliary cooling air conduit 94 supplies cooling air 59 to the vacuum air inlet 96 of the first blower 46, as described in more detail below.

In the preferred embodiment, the vacuum blower fan units 42, 44 are AMETEK "Windjammer" DC brushless DC motor-driven blowers identified as Model No. 116632-01 which operate on 120 volt AC (50/60 Hz, 4.5 amps) and are manufactured by Lamb Electric Division, Kent, Ohio. The power unit subassembly 40 generates a vacuum force of approximately 7 inches of Mercury at the first vacuum inlet 96. However, it is understood by those skilled in the art from this disclosure that the present invention is not limited to a vertical, two-stage vacuum system as described above. Single or multi-stage vacuum systems utilizing 120 volt or 230 volt AC single-phase or three-phase electric motors or other types of motors drivingly connected to various types of vacuum pumps or blowers mounted in a variety of configurations may be used to generate the suction force. Moreover, it is similarly understood that the use of an intake air filter and an exhaust muffler is not required depending on the particular application and the level of equipment noise that is acceptable.

Figure 3:
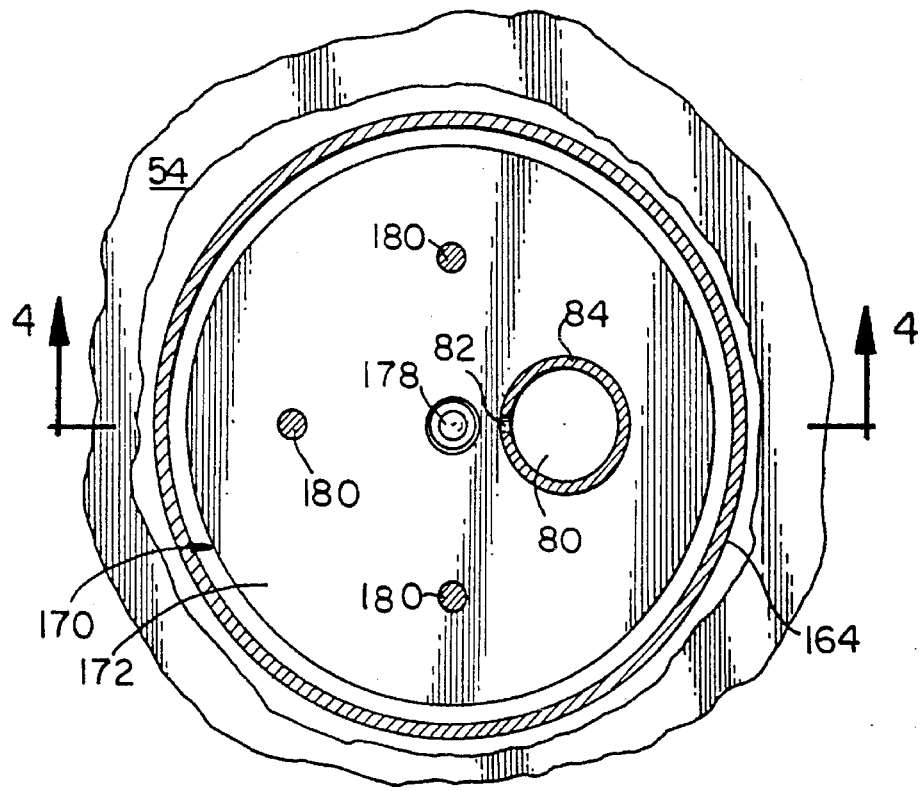
FIG. 3 is a cross-sectional view, partially broken away, of a collection tank cover of the vacuum apparatus shown in FIG. 2 taken along lines 3—3 of FIG. 2.

Referring now to FIGS. 1, 2 and 3, a tank 56 for holding the fluid to be vacuumed is provided. A cover 54 is secured to the top of the tank 56. The cover 54 supports the shroud 28 via the brackets 81. The power unit subassembly 40 is supported on a resilient pad 76 sandwiched between the base of the first blower 46 and the cover 54 for damping motor vibration and providing a vacuum seal. The tank 56 has a vacuum port 78 in fluid communication through a passage 80 with the vacuum generating source 12 for creating a first suction force in the tank 56. The passage 80 is formed by a relief tube 84 having a wall 83 and an opening 86 which extends into the tank 56.

As shown in FIGS. 1 and 2, the tank 56 further includes an inlet 162 in fluid communication with the fluid to be vacuumed and a drainage opening 160 for emptying fluid held within the tank 56. A check valve 168 is provided in fluid communication with the drainage opening 160 for preventing drained fluid from being drawn back into the tank 56.

Referring now to FIG. 1, a baffle 164, having a series of vertically aligned ports 166 which extend longitudinally along the baffle 164 in a diametrically opposed relation to the inlet 162, is located in the tank 56. The baffle 164 prevents the fluid, and any waste particles therein, from being drawn directly into the vacuum port opening 78.

In the presently preferred embodiment, the tank 56 is cylindrical in form and has a volume of approximately fifteen gallons. Preferably, the tank 56 is made from PVC. The relief tube 84 is made from 1 ½ inch diameter Schedule 40 PVC pipe. However, it is understood by those skilled in the art from this disclosure, that the tank 56 and the relief tube 84 may take various forms. For example, the tank 56 may be a rectilinear structure. Additionally, it is understood that the tank may be made from other materials, such as stainless steel or glass, if desired, to meet the requirements for a particular application, such as the collection of corrosive fluids. It is similarly understood that the shape and location of the relief tube 84 can be varied, if desired, to suit particular applications.

Figure 4:
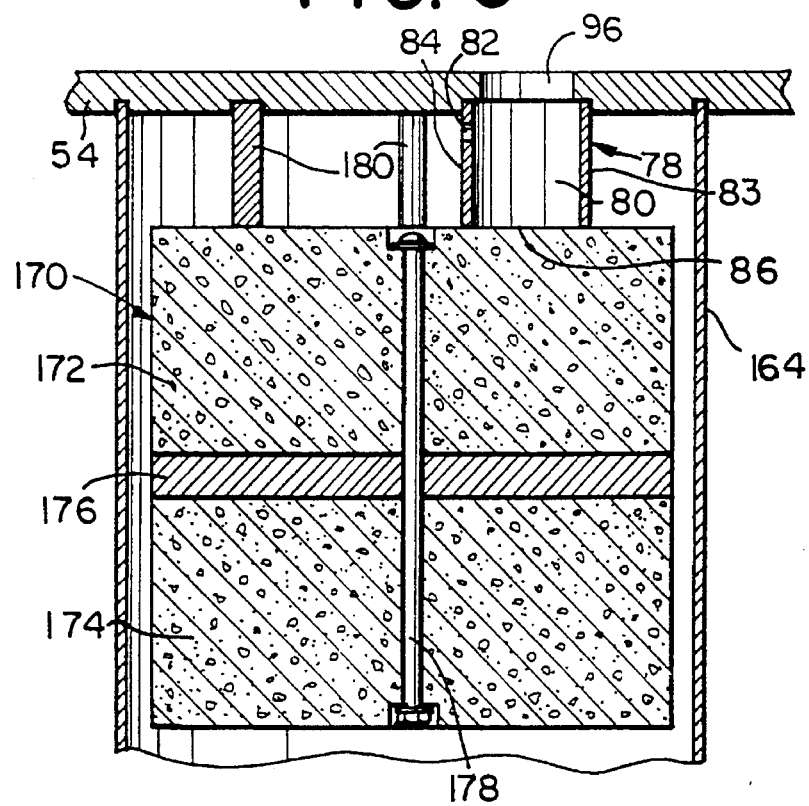
FIG. 4 is a cross-sectional view of a float of the vacuum apparatus taken along lines 4—4 in FIG. 3.

Referring now to FIGS. 1 and 4, in the presently preferred embodiment, a float 170 is located in the tank 56 for closing off the vacuum port 78 to prevent the fluid within the tank 56 from passing through the vacuum port 78. The float 170 is maintained in alignment with the vacuum port 78 by the baffle 164 and has a positive buoyancy with respect to the fluid such that the float 170 rises as the tank 56 is filled with the fluid to be vacuumed and falls as the fluid within the tank 56 is drained from the tank 56. The float 170 is positioned within the tank 56 such that when the fluid within the tank 56 is above a predetermined level, the suction force at the vacuum port 78 and the float buoyancy maintain the float 170 in a blocking position (as shown in FIG. 4) to at least partially block the vacuum port 98 creating a second suction force, which is less than the first suction force in the tank 56, as discussed below.

In the presently preferred embodiment, the float 170 is cylindrical in form and includes an upper float disk 172 and a lower float disk 174 which are made of a material which has a positive buoyancy with respect to the fluid to be collected. A weight 176, having a negative buoyancy with respect to the fluid to be collected, is located between the upper and lower disks 172 and 174 of the float assembly 170. The weight 176 is used to adjust the overall buoyancy of the float assembly 170 with respect to the fluid to be collected. The upper and lower portions 174, 174 of the float 170 and the weight 176 are assembled together as a unitary assembly by a fastener 178, preferably a bolt.

The float 170 has a buoyancy force $F_B$, with respect to the fluid being collected, and the vacuum port 78 has a suction force $F_S$. The float 170 has a weight W which is defined by the following formula:

$$F_S < W < F_B.$$

Adjusting the weight of the float to meet this requirement is important to the operation of the vacuum apparatus. The float weight W must be greater than the suction force $F_S$ or the float 170 will not release from the vacuum port until the vacuum generating source 12 is deactivated. The buoyancy force $F_B$ must be greater than the float weight W for the float 170 to block the vacuum port 78 when the fluid level rises.

In the preferred usage in a dental operatory, foaming agents are sometimes vacuumed along with the other fluids. Foam may rise to the vacuum port 78 within seconds, and the float 170 is buoyant enough to automatically rise with the foam to close off the vacuum port 78 to prevent any foam or fluid from causing damage to the vacuum motor fan units 42, 44.

In the preferred embodiment, the upper and lower float portions 172, 174 are approximately 9 inches in diameter and 3 inches thick, and are made of a light weight closed cell foam of a material type suitable for the application. The weight 176 is made from PVC sheet. The float 170 has a weight in the range of 3 to 28 ounces, and is preferably between 3 and 10 ounces. It is understood by those skilled in the art from this disclosure, that the weight of the float and its volume will depend on the density of the fluid to be vacuumed and the amount of suction force generated by the vacuum generating source 12. Moreover, the shape and size of the float 170 may be varied to suit particular applications. For example, the float 170 may be rectilinear or oval, and the float 170 may be sized to fit inside various baffle 164 shapes or to the interior walls of a tank 56 without a baffle. Additionally, the float 170 may be manufactured as a single molded part having the desired weight, or may be assembled from several pieces to have the desired weight. The float 170 may also be made as a sealed, hollow metal or plastic vessel to suit particular applications.

Referring now to FIGS. 3 and 4, a plurality of float stops 180 are mounted in the tank 56 which maintain a surface of the float 170 in parallel relation to the relief tube opening 86. The float stops 180 are attached to the tank cover 54 in a position above the float 170. The float stops 180 extend into the tank 56 the same distance as the relief tube 84. As best shown in FIG. 3, three float stops 180, spaced at 90° intervals from the relief tube 84, maintain the upper surface of the float 170 level when it reaches the blocking position (shown in FIG. 4). In the presently preferred embodiment, the float stops 180 are formed from ½ inch diameter by up to 4 inches long PVC rod. However, it is understood by those skilled in the art from this disclosure that the float stops 180 could have various configurations, and can be mounted in various positions to keep the upper surface of the float 170 level when it is in the blocking position. For example, the float stops 180 could extend laterally from the baffle 164 or a different number or form of float stops 180 could be utilized, if desired, to suit particular applications.

The vacuum generating source 12 creates a port suction force at the vacuum port 78, and the passage 80 includes a vacuum by-pass opening 82 which reduces the vacuum port 78 suction force when the float 170 is in the blocking position. As previously noted, the passage 80 is comprised of a relief tube 84 having a wall 83 and an opening 86 which extends into the tank 56 in alignment with the float 170, and the wall 83 includes a vacuum by-pass opening 82 extending therethrough. In the preferred embodiment, the vacuum bypass opening 82 is approximately 0.161 to 0.180 inches in diameter. However, it is understood by those skilled in the art from this disclosure that the size and location of the vacuum by-pass opening 82 can be varied, if desired, to suit particular applications. For example, the vacuum by-pass opening 82 could extend through the wall 83 at a higher position, in communication with a complementarily positioned vacuum relief port formed in the cover 54, or be connected directly to the auxiliary cooling air conduit 94.

Having provided a description of the structure of the vacuum apparatus 10, a brief description of its operation follows. The vacuum generating source 12 is operated to draw the fluid to be vacuumed into the tank 56. Fluid is drawn from the evacuation hoses in the dental operatories through the piping system connected to the tank inlet 162 and into the tank 56.

Assuming that the vacuum apparatus 10 has an empty tank 56 and none of the evacuation hoses are on, the vacuum generating source 12 is activated by providing power to the motors 50, 52 of the vacuum motor fan units 42, 44, respectively. The motor 50 of the first vacuum motor fan unit 42 turns the blower 46 in the blower chamber 108, creating a port suction force at the vacuum air inlet 96. Simultaneously, cooling air, represented by the arrows 59, is drawn through the intake fitting 71 and the air filter assembly 26 into the cooling air supply pipe 88. The vacuum relief valve 94 is in the full open position, and cooling air 59 is drawn through the lower portion 98 of the conduit 94 and the tank 56 into the first blower chamber 108 by the first blower 46. The cooling air is exhausted through the vacuum air outlet 62, through the blower interconnect conduit 102, directly to the vacuum air inlet 64 of the second vacuum motor fan unit 44. The blower 48 of the second vacuum motor fan unit 44 is being simultaneously rotated by the motor 52 in the second blower chamber 110, drawing the cooling air 59 from the first vacuum motor fan unit 42 through the blower interconnect 102 to increase the port suction force at the first vacuum air inlet 96. Cooling air 59 is also drawn through the upper portion 104 of the conduit 94 to the blower interconnect conduit 102 for the second blower 48. The cooling air 59 is exhausted from the second blower chamber 110 of the second vacuum motor fan unit 44 through the vacuum air outlet 114, connected to the exhaust line 112 which exhausts the cooling air 59 through the muffler 122.

Simultaneously, the cooling air 59 is drawn through the laterally projecting conduit 90 into the plenum chamber 70 between the opposed vacuum motor fan units 42, 44. The rotating motors 50, 52 turn cooling fans 124, 126 to draw the cooling air 59 through cooling air inlets 58, 60 into the motor chambers 132, 134. The cooling air 59 is then discharged through the motor air outlets 136, 138 inside the shroud 28.

The vacuum generating source 12 creates a first suction force in the tank 56 through the vacuum port 78. As the evacuation hoses in the dental operatories are turned on, the first suction force draws the fluid to be vacuumed into the evacuation hoses, through the piping system and into the tank 56 through the inlet 162. The fluid to be vacuumed and air, represented by the shaded arrows 61, are drawn into the tank 56. The fluid is deflected by the baffle 164 and falls to the bottom of the tank 56. The air 61 is then drawn through the ports 166 in the baffle 164, the vacuum port 78 and the first vacuum air inlet 96 into the first blower chamber 108 by the blower 46, along with the cooling air 59. The air mixture 59, 61 is exhausted through the vacuum air outlet 62 of the first blower chamber 108, through the blower interconnect duct 102 and drawn through the vacuum air inlet 64 into the second blower chamber 110 by the second blower 48. The air mixture 59, 61 is then exhausted from the second blower chamber 110 of the second vacuum motor fan unit 44 through the vacuum air outlet 114, connected to the exhaust line 112 which exhausts the air mixture 59, 61 through the muffler 122. As the evacuation hoses in additional operatories are turned on, the relief valve 92 is closed to reduce the flow of cooling air 59 to the blowers 46, 48 and increase suction at the tank inlet 162. The relief valve 92 closes in response to a decrease in the vacuum pressure in the tank 56 as additional evacuation hoses are turned on. As the relief valve 92 closes, the air mixture 59, 61 is mainly comprised of the air 61 drawn into the tank 56 with the fluid to be vacuumed.

The first suction force within the tank 56 acts on the fluid in the tank 56 to prevent the fluid from passing through the drainage opening 160 and the check valve 168. That is, the first suction force maintains the check valve 168 in a closed position to prevent back flow into the tank.

The float 170, which has a positive buoyancy with respect to the fluid in the tank 56, rises with the level of the fluid as it is collected in the tank 56, thereby detecting the level of the fluid within the tank 56. When the fluid within the tank 56 reaches a predetermined level (i.e., when the tank 56 is filled to capacity with fluid), the port suction force at the vacuum port 78 and the float buoyancy maintain the float 170 in a blocking position (as shown in FIG. 4) to at least partially block the main passage opening 86 of the vacuum port 78 when the fluid reaches the predetermined level to prevent the fluid from entering the vacuum port 78. When the float 170 is in the blocking position, a second suction force is created in the tank 56, which is less than the first suction force in the tank 56. With the float 170 in the blocking position, the port suction force, which creates the first suction force in the tank 56, is now acting on the upper surface of the float 170, against the float weight. The combination of the port suction force and the buoyancy of the float 170 maintain the float 170 in the blocking position, creating a vacuum blockage. The second suction force in the tank 56 is created only by the limited flow of air 59, 61 through the vacuum by-pass opening 82 or air 59,61 drawn through the gaps between the float 170 and the relief tube opening 86. The second suction force is much lower than the first suction force, and can be nearly zero if the vacuum by-pass opening 82 is connected directly to the cooling air conduit 94.

The second suction force is not sufficient to maintain the fluid in the tank 56, and the weight of the fluid within the tank 56 forces the check valve 168 to open, draining the fluid from the tank 56. The fluid is then drained, thereby causing the float 170 to move from the blocking position when the fluid in the tank 56 is at a level below the predetermined level, to restore the first suction force in the tank 56.

The port suction force that acts on the float 170 drops when the float 170 blocks the passage opening 86 because of the vacuum by-pass opening 82. When the main opening 86 of the vacuum port 78 is blocked, the volume of air passing through the by-pass opening 82 increases. This air flow causes the port suction force on the float 170 to drop, and also provides an opening for supplying cooling air to the blower side of the first vacuum motor fan unit 42. The float 170 moves from the blocking position because as the fluid level in the tank 56 drops, the port suction force at the passage opening 86 is not sufficient to hold the weight of the float 170 without the buoyancy force. With the float 170 removed from the blocking position, the first suction force through the vacuum port 78 is re-established in the tank 56, and vacuum service to the dental operatories is restored. The first suction force is sufficient to again close the check valve 168.

The entire drainage operation is accomplished while continuously operating the vacuum generating source 12 and drains approximately one gallon of fluid from the tank 56 in approximately 15 seconds. The amount of fluid drained in one cycle is determined by the tank size, the float weight and the liquid level for a given suction force. The cycle repeats after another gallon of liquid enters the tank. Vacuum service is therefore only interrupted for a short period of time, eliminating the longer interruptions which were prevalent with the previous systems. After the close of business hours, all of the evacuation hoses are turned off and the vacuum generating source is turned off. Without any suction force acting on the fluid in the tank 56, the check valve 168 opens and the fluid in the tank 56 drains.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An automatically draining vacuum apparatus for collecting a fluid to be vacuumed comprising:

a vacuum generating source;

a tank for holding the fluid to be vacuumed, the tank having a vacuum port in fluid communication through a passage with the vacuum generating source for creating a suction force of a first magnitude in the tank, an inlet in fluid communication with the fluid to be vacuumed, and a drainage opening for emptying fluid held within the tank, the suction force drawing the fluid to be vacuumed into the tank through the inlet and preventing the fluid within the tank from passing from the tank through the drainage opening;

a float located in the tank for closing off the vacuum port to prevent the fluid within the tank from passing through the vacuum port, the float having a positive buoyancy with respect to the fluid such that the float rises as the tank is filled with the fluid to be vacuumed and falls as the fluid within the tank is drained from the tank, the float being positioned within the tank such that when the fluid within the tank is above a predetermined level, the suction force at the vacuum port and the float buoyancy maintain the float in a blocking position to at least partially block the vacuum port creating a reduced suction force having a second magnitude which is less than the first magnitude of the suction force in the tank, the suction force of the second, reduced magnitude allowing the fluid within the tank to drain to a level below the predetermined level thereby causing the float to move from the blocking position to restore the suction force in the tank to the first magnitude;

the passage being comprised of a relief tube having a wall and an opening which extends into the tank in alignment with the float, and the wall includes a vacuum by-pass opening extending therethrough; and a plurality of float stops mounted in the tank which maintain a surface of the float in a parallel relation to the relief tube opening.

2. The apparatus of claim 1 further comprising a check valve in fluid communication with the drainage opening for preventing drained fluid from being drawn back into the tank.

3. The apparatus of claim 1 wherein the vacuum generating source creates a port suction force at the vacuum port vacuum by-pass opening reduces the port suction force when the float is in the blocking position.

4. The apparatus of claim 3 wherein the vacuum by-pass opening is approximately 0.161 to 0.180 inches in diameter.

5. The apparatus of claim 1 wherein the float has a buoyancy force $F_B$ and the vacuum port has a suction force $F_S$, the float has weight W which is defined by the following formula:

$$F_S < W < F_B.$$

6. The apparatus of claim 1 wherein the float has a weight of approximately 3 to 28 ounces.

7. An automatically draining vacuum apparatus for collecting a fluid for a dental operatory comprising:

a vacuum generating source;

a tank for holding the fluid to be vacuumed, the tank having a vacuum port in fluid communication through a passage with the vacuum generating source for creating a suction force of a first magnitude in the tank, an inlet in fluid communication with the fluid to be vacuumed, and a drainage opening for emptying fluid held within the tank, the suction force drawing the fluid to be vacuumed into the tank through the inlet and preventing the fluid within the tank from passing from the tank through the drainage opening;

a float located in the tank for closing off the vacuum port to prevent the fluid within the tank from passing through the vacuum port, the float having a positive buoyancy with respect to the fluid such that the float rises as the tank is filled with the fluid to be vacuumed and falls as the fluid within the tank is drained from the tank, the float being positioned within the tank such that when the fluid within the tank is above a predetermined level, the suction force at the vacuum port and the float buoyancy maintain the float in a blocking position to at least partially block the vacuum port creating a reduced suction force having a second magnitude which is less than the first magnitude of the suction force in the tank, the suction force of the second, reduced magnitude in the tank allowing the fluid within the tank to drain to a level below the predetermined level thereby causing the float to move from the blocking position to restore the suction force in the tank to the first magnitude;

the vacuum port being comprised of a relief tube having a wall and an opening which extends into the tank in alignment with the float, and the wall includes a vacuum by-pass opening extending therethrough; and a plurality of float stops mounted in the tank which maintain a surface of the float in a parallel relation to the relief tube opening.

8. The apparatus of claim 7 further comprising a check valve in fluid connection with the drainage opening for preventing drained fluid from being drawn back into the tank.

9. The apparatus of claim 7 wherein the vacuum generating source creates a port suction force at the vacuum port vacuum by-pass opening reduces the port suction force when the float is in the blocking position.

10. The apparatus of claim 9 wherein the vacuum by-pass opening is approximately 0.161 to 0.180 inches in diameter.

11. The apparatus of claim 7 wherein the float has a buoyancy force $F_B$ and the vacuum port has a suction force $F_S$, the float has a weight W which is defined by the following formula:

$$F_S < W < F_B.$$

12. The apparatus of claim 7 wherein the float has a weight of approximately 3 to 28 ounces.

* * * * *